(12) United States Patent
Stolz et al.

(10) Patent No.: US 8,948,882 B2
(45) Date of Patent: Feb. 3, 2015

(54) FIXATION COMPONENTS FOR IMPLANTABLE MEDICAL DEVICES AND ASSOCIATED DEVICE CONSTRUCTION

(75) Inventors: Brian T. Stolz, Bloomington, MN (US); Carole A. Tronnes, Stillwater, MN (US)

(73) Assignee: Medtronic, Inc., Minneapolis, MN (US)

( * ) Notice: Subject to any disclaimer, the term of this patent is extended or adjusted under 35 U.S.C. 154(b) by 559 days.

(21) Appl. No.: 13/216,663

(22) Filed: Aug. 24, 2011

(65) Prior Publication Data

US 2012/0053665 A1    Mar. 1, 2012

Related U.S. Application Data

(60) Provisional application No. 61/376,963, filed on Aug. 25, 2010.

(51) Int. Cl.
  *A61N 1/18*    (2006.01)
  *A61N 1/05*    (2006.01)

(52) U.S. Cl.
  CPC .................................... *A61N 1/0558* (2013.01)
  USPC ............ 607/126; 607/117; 607/118; 607/122

(58) Field of Classification Search
  CPC ....... A61B 5/6839; A61N 1/558; A61N 1/057
  USPC ........................................................ 607/126
  See application file for complete search history.

(56) References Cited

U.S. PATENT DOCUMENTS

| | | |
|---|---|---|
| 5,300,107 A | 4/1994 | Stokes |
| 5,531,781 A | 7/1996 | Alferness |
| 6,188,932 B1 | 2/2001 | Lindegren |
| 6,240,322 B1 | 5/2001 | Peterfeso |
| 6,999,819 B2 | 2/2006 | Swoyer |
| 7,330,764 B2 | 2/2008 | Swoyer |
| 2006/0036307 A1* | 2/2006 | Zarembo et al. .............. 607/122 |
| 2006/0095078 A1 | 5/2006 | Tronnes |
| 2008/0183257 A1* | 7/2008 | Imran et al. ................... 607/117 |
| 2010/0108077 A1* | 5/2010 | Lindh et al. ................... 128/848 |
| 2010/0256696 A1* | 10/2010 | Schleicher et al. ............... 607/2 |

* cited by examiner

*Primary Examiner* — Christopher D Koharski
*Assistant Examiner* — Natasha Patel

(57) ABSTRACT

A fixation component for a medical electrical lead includes a tubular sidewall that has an outer surface from which a plurality of deformable barb-like projections extend, each projection being in proximity to an aperture that extends through the sidewall. The projections are spaced apart from one another along a length of the component, and each extends from a first end, attached to the sidewall, in proximity to an edge of the corresponding aperture, to a second, free end, spaced apart from the outer surface of the sidewall, when the projection is un-deformed. The outer surface of the sidewall preferably includes reduced diameter end portions, to maintain a relatively low profile, when tubing members overlap thereon to secure the component around a body of the medical electrical lead. The body of the lead may include a conductor coil whose outer surface is directly overlaid by the component.

25 Claims, 4 Drawing Sheets

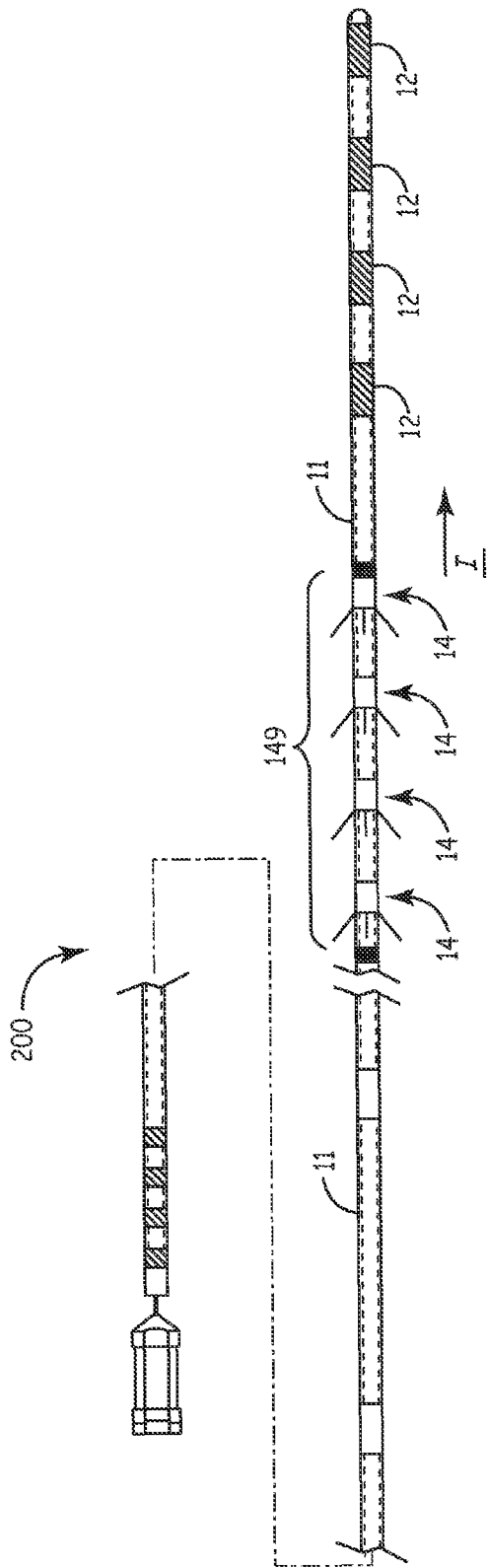
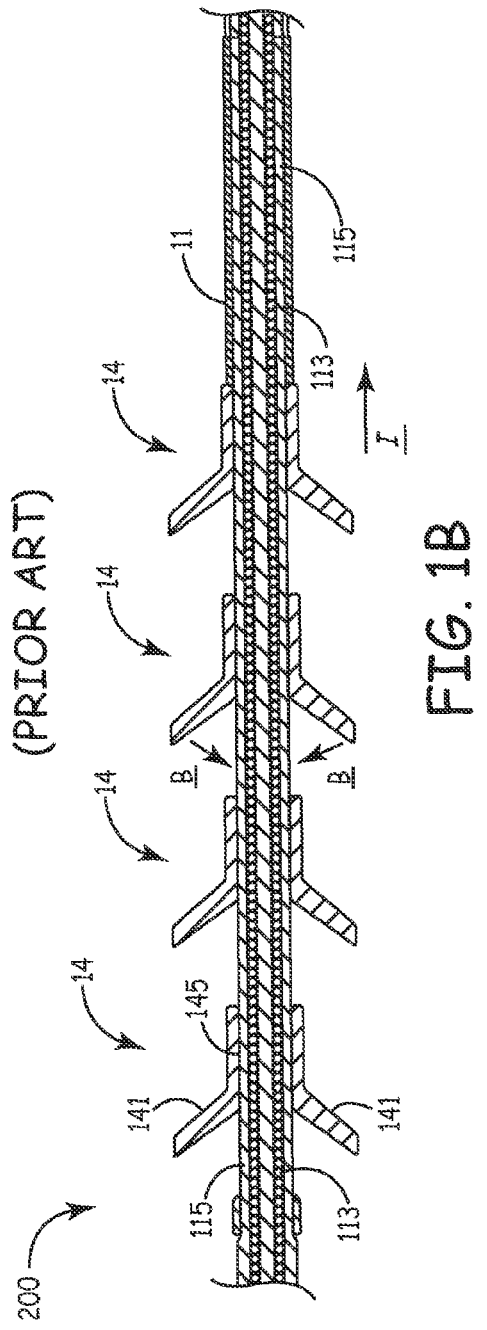
FIG. 1A (PRIOR ART)
FIG. 1B (PRIOR ART)

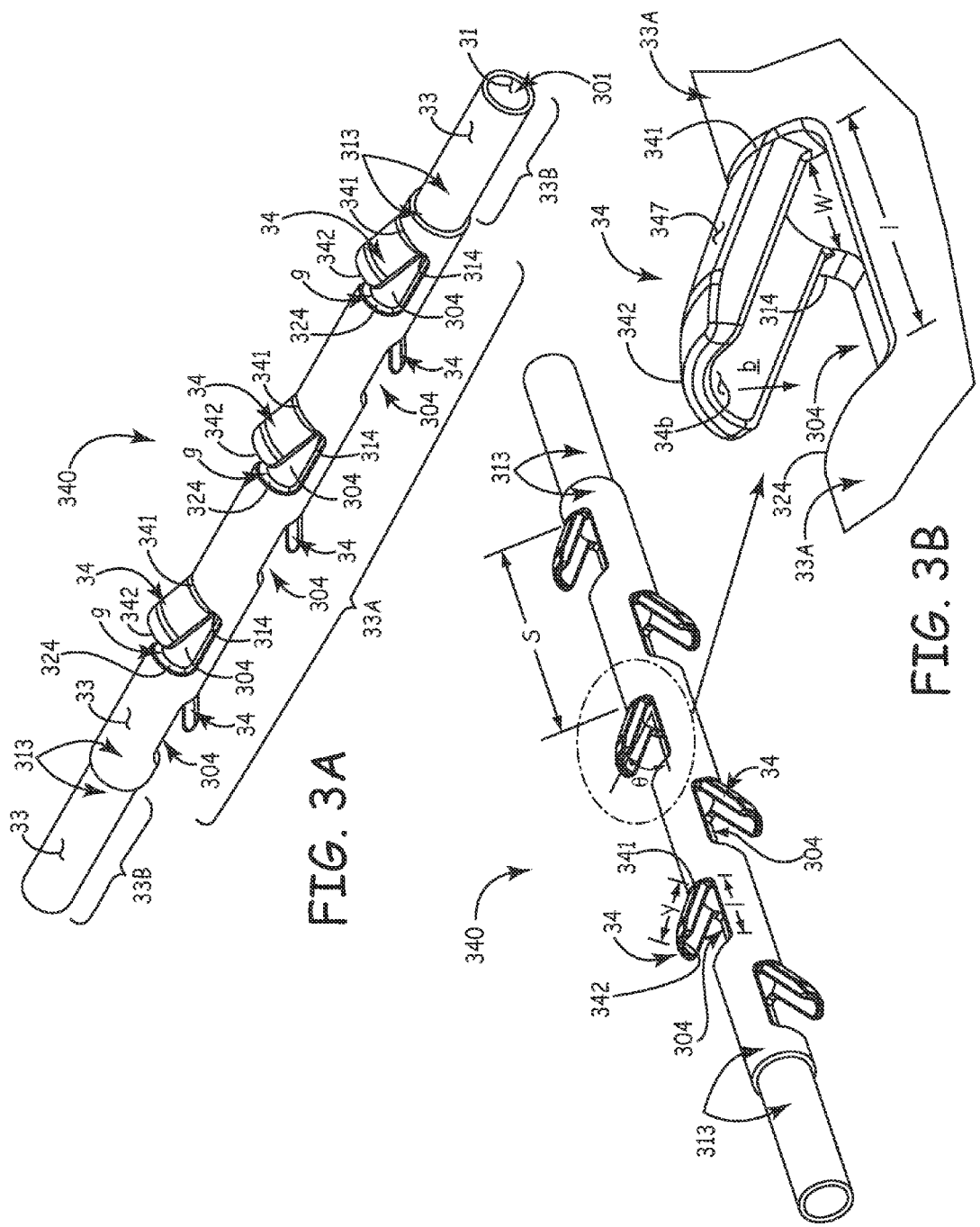

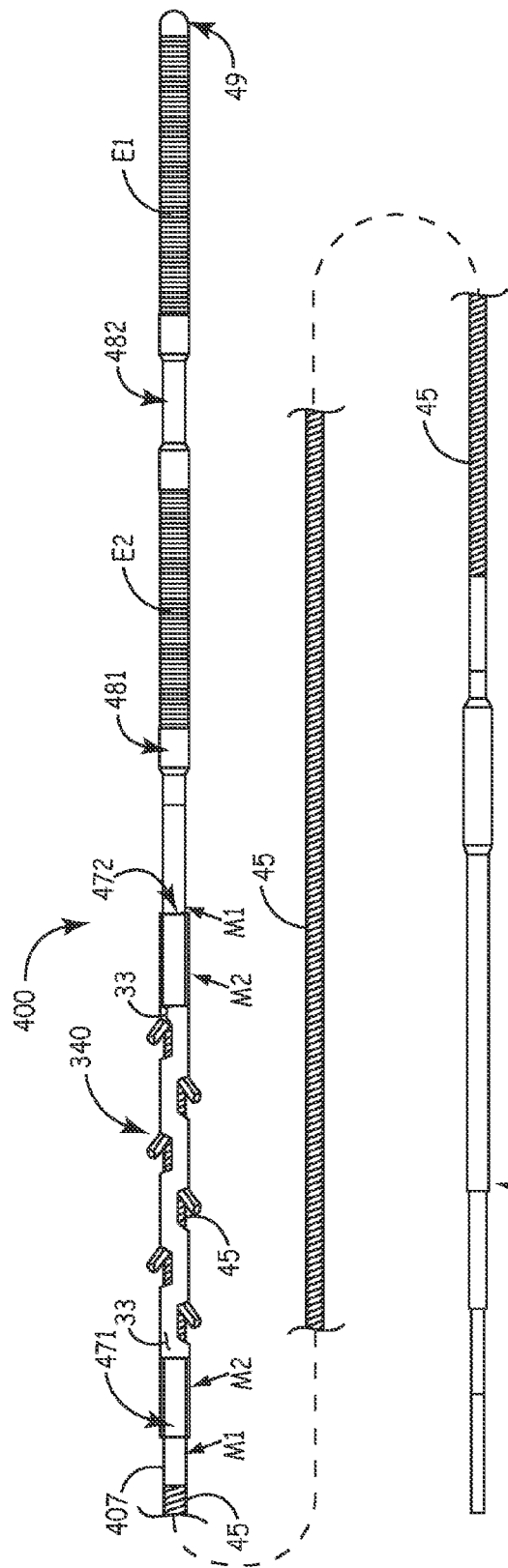
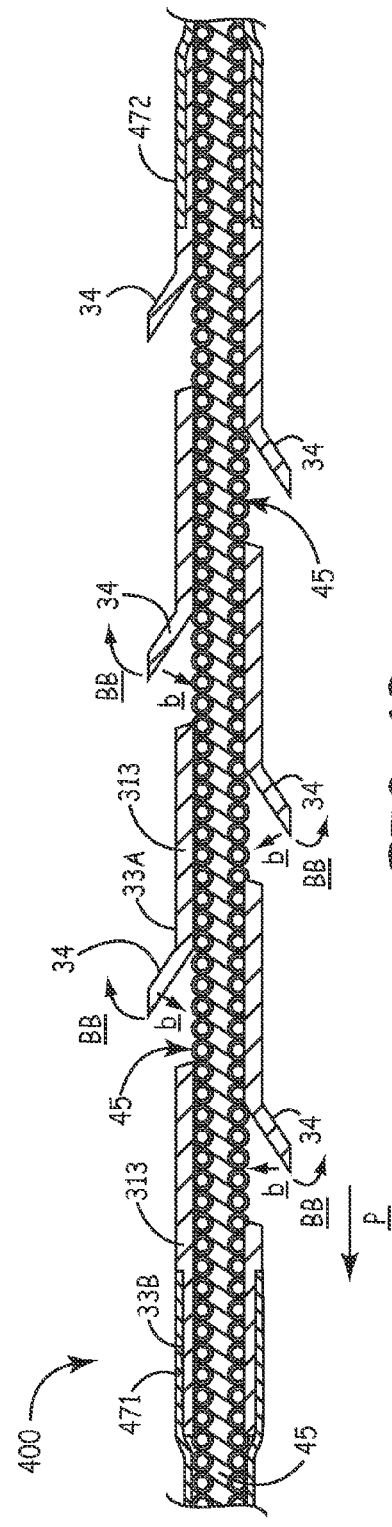
FIG. 4A
FIG. 4B

FIXATION COMPONENTS FOR IMPLANTABLE MEDICAL DEVICES AND ASSOCIATED DEVICE CONSTRUCTION

CROSS-REFERENCE TO RELATED APPLICATIONS

The present application claims priority to U.S. Provisional Patent Application No. 61/376,963, filed Aug. 25, 2010, which application is hereby incorporated by reference as if re-written in its entirety.

TECHNICAL FIELD

The present disclosure pertains to components and constructions for implantable medical devices and more particularly to those related to fixation.

BACKGROUND

Implantable medical devices, for example, electrical leads, typically include fixation features that are designed to hold the device in place at an implant site, within a body of a patient, in order to facilitate the collection of diagnostic information at, or the delivery of therapy to the site. One example of an implantable medical electrical lead 200 that includes fixation features is the Model 3889 quadripolar lead, available from Medtronic, Inc. for Interstim® Therapy, a representation of which is shown in the plan view of FIG. 1A. FIG. 1A illustrates a fixation feature 149 of this prior art lead 200 including a plurality of independent, tined elements or components 14, which are mounted around a body 11 of lead 200 and spaced apart from one another along a length of body 11, just proximal to electrodes 12. The construction of tined components 14 and of lead 200 can be similar to that described in commonly-assigned U.S. Pat. No. 6,999,819.

FIG. 1B is a longitudinal cross-section view through body 11, along a section thereof where tined components 14 are attached. FIG. 1B illustrates body 11 including an elongate conductor coil 113 surrounded by an outer insulation sheath 115, and each individual tined component 14 including a mounting band 145 that encircles sheath 115, being bonded thereto. Each tine 141 extends outward from the corresponding band 145, yet is relatively flexible to bend, for example, per arrow B, when the section of lead body 11 is inserted, per arrow I, into an introducer needle or sheath for the implantation of lead 200. Once the introducer needle/sheath is withdrawn from around fixation feature 149, tines 141 of each tined component 14 extend outward again to hold electrodes 12 of lead 200 in a relatively fixed implant position, for example, to stimulate sacral nerves, as is illustrated in the schematic of FIG. 2 (borrowed from the above-referenced '819 patent). With reference back to FIG. 1A, conductor coil 113 electrically couples each electrode to a corresponding connector contact of a proximal connector terminal 23 of lead 200.

With reference to FIG. 2, tines 141, once released from the constraint of the introducer needle/sheath, extend outward within the subcutaneous tissue and thereby prevent proximal dislodgement of lead 200, for example, per arrow P. It should be noted that the Model 3889/lead 200 is constructed for chronic implantation, but that a similar fixation feature may be employed by medical electrical leads that are intended for temporary implant, for example, to evaluate the efficacy of sacral nerve stimulation, like that described in the commonly-assigned and co-pending patent application entitled TEMPORARY IMPLANTABLE MEDICAL ELECTRICAL LEADS, filed on Apr. 14, 2010 as U.S. Provisional Patent Application No. 61/324,144, filed Apr. 14, 2010, now U.S. patent application Ser. No. 13/084,420, filed Apr. 11, 2011.

Although fixation features, for example, like feature 149, that are known in the art, have been found effective for holding an implanted medical device in place, there is still a need for new fixation components that can facilitate simpler device construction/assembly, for example, in order to reduce cost and/or increase repeatability in the manufacturing of relatively large volumes of the devices. Simpler device constructions can be particularly beneficial for relatively low profile devices that employ relatively small components, like the aforementioned temporary implantable leads.

BRIEF DESCRIPTION OF THE DRAWINGS

The following drawings are illustrative of particular exemplary embodiments and therefore do not limit the scope of the invention. The drawings are not to scale (unless so stated) and are intended for use in conjunction with the explanations in the following detailed description. Embodiments of the present disclosure will hereinafter be described in conjunction with the appended drawings, wherein like numerals denote like elements.

FIG. 1A is plan view of the prior art lead.

FIG. 1B is a longitudinal cross-section view through a portion of the prior art lead.

FIGS. 3A-B are perspective views of a fixation component, according to some embodiments.

FIG. 4A is a plan view of a temporary medical electrical lead that includes the fixation component of FIGS. 3A-B.

FIG. 4B is a longitudinal cross-section view through a portion of the temporary medical electrical lead of FIG. 4A.

DETAILED DESCRIPTION

Figure 2:
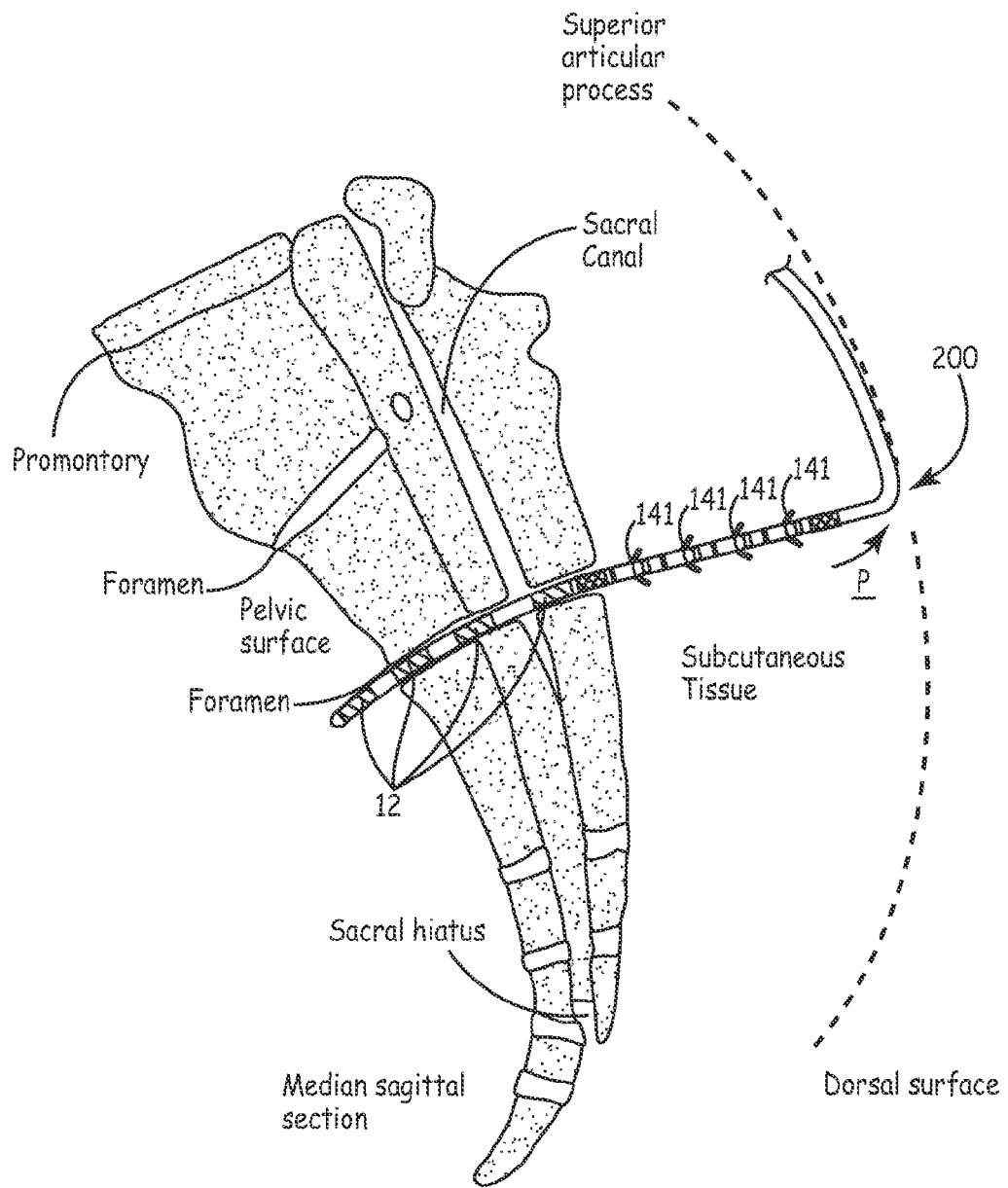
FIG. 2 is a schematic showing the lead implanted for sacral nerve stimulation.

The following detailed description is exemplary in nature and is not intended to limit the scope, applicability, or configuration of embodiments disclosed herein. Rather, the following description provides practical illustrations for implementing exemplary embodiments. Examples of constructions, materials, dimensions, and manufacturing processes are provided for selected elements, and all other elements employ that which is known to those of skill in the field of the disclosure. Those skilled in the art will recognize that many of the examples provided have suitable alternatives that can be utilized.

FIGS. 3A-B are perspective views of a fixation component 340, according to some embodiments, which may be mounted around a body of an implantable medical device, for example, around body 11 of medical electrical lead 200 (FIG. 1A), in place of the four individual tined components 14 of fixation feature 149. FIGS. 3A-B illustrate component 340 including an elongate tubular sidewall 313, a plurality of pre-formed fixation elements in the form of deformable barb-like projections 34 and an aperture 304 corresponding to each projection 34. FIG. 3A further illustrates tubular sidewall 313 including an inner surface 31 and an outer surface 33, wherein outer surface 33 is divided into a central portion 33A, from which each barb-like projection 34 extends outward, and two end portions 33B that extend longitudinally from either end of central portion 33A. According to preferred embodiments, inner surface 31 defines a lumen 301 that has a uniform diameter along an entire length of component 340, to receive a device body, for example, as will be described below in conjunction with FIGS. 4A-B, whereas each of end portions 33B of outer surface 33 has a smaller diameter than that of central portion 33A, in order to accommodate overlapping tubular members in the construction of a device, as will also be described below in greater detail.

According to the illustrated embodiment, each aperture 304 extends through tubular sidewall 313, from outer surface 33 to inner surface 31, and has a first edge 314 located in proximity to a first end 341 of the corresponding deformable barb-like projection 34, which first end 341 is attached to tubular sidewall 313. Each barb-like projection 34 is shown extending, at an angle θ, from first end 341 to a second, free end 342 thereof. With further reference to an enlarged detail view of a circled portion of component 340 in FIG. 3B, a length l and a width w of aperture 304 are designated; and, according to preferred embodiments, length l and width w of each aperture 304 are sized so that each aperture 304 receives the corresponding projection 34 therein, when the projection 34 bends inward, per arrow b. The deformation/bending of projections 34 will be described below, in conjunction with FIGS. 4A-B.

With further reference to FIGS. 3A-B, the plurality of barb-like projection 34 of component 340 are shown spaced apart from one another along a length of central portion 33A of outer surface 33 of tubular sidewall 313, and arranged into two longitudinally extending columns, which are displaced circumferentially from one another so that all the projections 34 of the first column extend outward in a first direction and all the projections 34 of the second column extend outward in a second direction, which is opposite the first direction. FIGS. 3A-B further illustrate the first column of barb-like projections 34 longitudinally displaced from the second column of barb-like projections 34 resulting in a staggered arrangement of the plurality of projections 34. It should be noted that, embodiments of the present disclosure should not be limited to the particular arrangement of the plurality of projections 34 which is shown in the FIGs., and that alternate arrangements may include, for example, a single column, or more than two columns, or a more random arrangement of projections 34. According to some alternate embodiments, columns of deformable barb-like projections 34 are aligned, however, an advantage of a staggered arrangement, like that shown in FIGS. 3A-B, is an increased area of the wall section of tubular sidewall 313 that surrounds each aperture 304, which may lend more structural integrity to component 340, and may facilitate the manufacturing, for example, via injection molding, of relatively small diameter embodiments of component 340, as will be described below. According to an exemplary embodiment, the length of central portion 33A is greater than approximately 0.5 inch (17.7 mm), and may be up to approximately one inch (25.4 mm), for example, to provide an extent of the plurality of projections 34 that is useful for fixation of a device such as lead 200 (FIG. 1A), when chronically implanted for sacral nerve stimulation, according to the schematic of FIG. 2, or for similar fixation of a temporary medical electrical lead 400, which is shown in FIGS. 4A-B, when temporarily implanted to evaluate the efficacy of sacral nerve stimulation.

FIG. 4A is a plan view of medical electrical lead 400 that includes fixation component 340; and FIG. 4B is a longitudinal cross-section view through a portion of lead 400. Dashed lines in FIG. 4A represent the extent of lead 400 between elongate sections thereof. FIG. 4A illustrates lead 400 including a proximal connector terminal 43, two distal electrodes E1, E2 and an elongate body formed, at least in part, by a conductor coil 45 which extends from connector terminal 43 to distal electrodes E1, E2 and which electrically couples each of two contacts of connector terminal 43 to the corresponding electrode E1, E2. According to some preferred embodiments, conductor coil 45 includes a pair of insulated wire filars wound to form an elongate lumen that extends along a length of lead 400, for example, to accommodate a stylet which is used when implanting lead 400, according to methods known in the art. Each insulated wire filar includes an insulative layer (i.e. coating or jacket) for electrical isolation. According to an exemplary embodiment, each wire filar is a cable that has a diameter of approximately 0.01 inch (0.254 mm), and that includes seven wire strands of a stainless steel alloy (304L or 316L), wherein each strand has a diameter of approximately 0.002 inch (0.05 mm), and each insulative layer is ethylene tetrafluoroethylene (ETFE). However, a number suitable alternatives for the wire filars and corresponding insulative layers are known to those skilled in the art. FIGS. 4A-B further illustrate fixation component 340 directly overlaying an outer surface of conductor coil 45 and positioned proximal to distal electrodes E1, E2. According to the illustrated embodiment, component 340 is secured in place by a pair of tubular members 471, 472, each of which overlaps and closely conforms to a corresponding end portion 33B (FIG. 3B) of outer surface 33 of sidewall 313 of component 340. In addition, according to some embodiments, component 340 may be further secured in place by an interference fit thereof over coil 45, for example, as will be further described below.

With further reference to FIGS. 4A-B, it may be appreciated that the above-described smaller diameter of each end portion 33B of outer surface 33 allows the corresponding tubular member 471, 472 to overlap thereon without increasing the outer diameter of lead 400 beyond that of central portion 33A of outer surface 33 of sidewall 313 of the secured component 340. According to some preferred embodiments, tubular members 471, 472 are formed from a heat shrinkable material having a relatively thin wall, for example, between approximately 0.0003 inch (0.008 mm) and approximately 0.001 inch (0.025 mm), and heating of tubular members 471, 472, in order to conform members 471, 472 to conductor coil 45 and to corresponding end portions 33B, may be accomplished via the application of hot air, for example, from a hot air nozzle, or by any other suitable method known to those skilled in the art. A suitable example of a heat shrinkable material is polyester, for which biocompatible medical grades of shrink tubing are known to those skilled in the art. A length of each end portion 33B of outer surface 33 of tubular sidewall 313 of component 340 is preferably approximately 0.1 inch (2.54 mm) to accommodate the overlap of the corresponding tubular member 471, 472.

FIG. 4A further illustrates lead 400 including additional tubular members 481, 482 that overlay and closely conform to conductor coil 45 and corresponding ends of electrodes E1, E2, which members 481, 482 may also be formed from the aforementioned polyester shrink tubing, as described in commonly-assigned and co-pending patent application entitled TEMPORARY IMPLANTABLE MEDICAL ELECTRICAL LEADS, filed on Apr. 14, 2010 as U.S. Provisional Patent Application No. 61/324,144, filed Apr. 14, 2010, now U.S. patent application Ser. No. 13/084,420, filed Apr. 11, 2011, which is hereby incorporated by reference in its entirety. With reference to FIG. 2 of this incorporated application, according to some preferred embodiments of the present disclosure, fixation component 340 is substituted for the plurality of tine elements 140 of the lead 100, and tubular members 471, 472 employed rather than the tubular member 17 of the lead 100. Thus, according to some exemplary embodiments, each of tubular members 471, 472, 481 and 482 are, initially, all separate pieces of polyester shrink tubing; and, prior to being conformed, tubular members 471, 472 may have an outer diameter of approximately 0.032 inch (0.812 mm) and a wall thickness of approximately 0.001 inch (0.0254 mm), and tubular members 481, 482 may have an outer diameter of approximately 0.038 inch (0.965 mm) and a wall thickness of approximately 0.0005 inch. (0.013 mm)

According to some preferred embodiments, tubular member 471 extends proximally from component 340 to a proximal terminal end 407 thereof, over a limited length, in order to leave a portion of conductor coil 45 exposed to the subcutaneous environment external to lead 400, when lead 400 is implanted. As is described in the incorporated application (for the conductor coil 15 of the lead 100—FIG. 2), tissue ingrowth around the exposed subcutaneous portion of coil 45 can extend into the coil lumen and block the lumen from acting as a conduit for infection to spread into the patient's body from a more proximal portion of conductor coil 45 that extends outside the patients body, when lead 400 is temporarily implanted during the evaluation period. Furthermore, like the lead 100 of the incorporated application, lead 400 may further include radiopaque marking useful for positioning of lead 400 during implant and/or during follow-up, if fluoroscopy is employed for visualization. With reference to FIG. 4A alternative approximate locations for a pair of radiopaque marker bands, at either end of fixation component 340, are indicated by arrows M1 and M2. The optional marker bands may be formed from any suitable biocompatible and radiopaque material, examples of which include, without limitation, Pt/IR alloy, tantalum and barium sulfate-loaded or tantalum-loaded silicone rubber. According to some embodiments, a split sleeve, for example, formed from Pt/IR, may be placed around and then swaged directly onto conductor coil 45 at either end of component 340, so as to be positioned in between coil 45 and the corresponding overlying tubular member 471, 472 (as well as component 340, if at the M2 positions). Alternately, a silicone sleeve loaded with a radiopaque material, for example, barium sulfate or tantalum, may be placed directly onto coil 45 at either end of fixation component 340. According to some additional alternate embodiments, the radiopaque marking may be formed together with fixation component 340, for example, via loading component 340 with a radiopaque material, such as barium sulfate or tantalum, or insert molding component 340 around preformed radiopaque marker bands.

According to some preferred embodiments, a diameter of central portion 33A of outer surface 33 of sidewall 313 is no greater than approximately 0.04 inch (1.016 mm) so that lead 400 may be inserted, for implant, through an 18 gauge introducer needle (lumen diameter of approximately 0.044 inch (1.118 mm)). According to the illustrated embodiment of lead 400, as mentioned above, a maximum outer diameter of each overlapping and closely conforming tubular member 471, 472, is approximately flush with the diameter of central portion 33A of outer surface 33. Also, as pointed out above, component 340 preferably directly overlays the outer surface of conductor coil, such that a minimum wall thickness of sidewall 313 of fixation component 340, in order to keep lead 400 within the aforementioned maximum diameter, need not be so thin as to compromise the structural integrity thereof or the manufacturability thereof. Thus, as may be seen in FIGS. 4A-B, portions of the overlaid conductor coil 45 are exposed, through apertures 304 of component 340, to the subcutaneous environment external to implanted lead 400.

The flush transition between overlapping tubular members 471, 472 and central portion 33A can facilitate easier insertion of lead 400 through the introducer needle/sheath when implanting lead 400. Furthermore, when component 340 passes through the introducer needle/sheath, as lead 400 is inserted therethrough, each projection 34 is deformed to bend inward, per arrow b, and can be received within a perimeter of the corresponding aperture 304, to reduce an amount of drag at the interface between projections 34 and an inner surface of the needle/sheath. Additional optional features of each projection 34 may also serve the same purpose. For example, with reference again to the enlarged detail view of the circled portion of component 340, in FIG. 3B, according to some preferred embodiments, second, free end 342 of each projection 34 is tapered or thinned and each projection 34 has an arcuate cross-section that curves in a direction approximately orthogonal to an extension thereof between corresponding ends 341, 342, resulting in a concave inner surface 346 and a convex outer surface 347. Concave inner surface 346, preferably, generally conforms to around the outer diameter of conductor coil 45, and a maximum wall thickness of each projection is preferably no greater than that of sidewall 313, along central portion 33A of outer surface 33, so that convex outer surface 347 may become approximately flush with central portion 33A of outer surface 33, when projection 34 is bent inward within introducer needle/sheath, if the introducer needle/sheath has a lumen diameter that approaches, or is approximately equal to, the diameter of central portion 33A of outer surface 33. Although not shown in the FIGs., the wall thickness of each projection 34, in proximity to the corresponding first, attached end 341, may be thinned in order to facilitate bending, per arrow b.

It should be noted that, in addition to providing a space to receive each inwardly bent barb-like projection 34, during insertion of lead 400 through the introducer needle/sheath, each aperture 304 of fixation component 340 provides additional space for subcutaneous tissue to surround and engage the corresponding projection 34 for fixation, upon withdrawal of the introducer. Furthermore, a perimeter of each aperture 304 may be enlarged beyond that which is necessary to receive the corresponding bent projection 34 in order to provide even more space for the tissue to surround and engage each projection 34 for fixation. Alternately, or in addition a thickness of portions of sidewall 313, which are immediately adjacent to and define a second edge 324 of each aperture 304, may be thinned to also facilitate the engagement of tissue around each projection 34.

According to some preferred embodiments, fixation component 340 is formed from a medical grade liquid silicone rubber (LSR), for example, by means of injection molding methods that are known in the art. The use of LSR allows for the repeatable manufacture of certain preferred embodiments of component 340, which have relatively thin wall sections, for example, with reference to FIG. 3A: a nominal thickness of sidewall 313 along central portion 33A of outer surface 33 is approximately 0.006 inch (0.152 mm, as is a nominal wall thickness of each projection 34; a nominal thickness of sidewall 313 along end portions 33B of outer surface 33 is between approximately 0.003 inch (0.076 mm) and approximately 0.004 inch (0.102 mm) and a diameter of lumen 301 may be between approximately 0.023 inch (0.584 mm) and approximately 0.027 inch (0.685 mm) to directly overlay, for example, in an interference or approximate line-to-line fit, the outer surface of conductor coil 45, which has a diameter of approximately 0.025 inch (0.635 mm). Thus, the exemplary embodiment of component 340 maintains the above-defined preferred profile for lead 400, wherein the maximum diameter is no greater than approximately 0.04 inch (1.016 mm) to fit within an 18 gauge introducer needle, and the above-described exemplary tubing members 471, 472 are heat shrunk over end portions 33B to secure fixation component 340 in place without compromising the profile. As mentioned above, an interference fit of component 340, according to some embodiments, further serves to secure component 340 in place; and those skilled in art will appreciate that heptane may be used to swell component 340, when component 340 is formed from silicone rubber, in order to assemble component 340 around coil 45 for the interference fit thereover. It should be noted that, according to some alternate embodiments, component 340 may have relatively thicker wall sections, than those indicated above, if the device that employs component 340, for example, a chronically implantable medical electrical lead, is not required to have the relatively low profile. These embodiments of component 340, having the relatively thicker wall sections, may be formed from other medical grade plastics, for example, polyurethane, which has been typically employed for various fixation components of medical electrical leads.

Since LSR is relatively soft (i.e. relatively low durometer) compared to some other materials that have been previously employed for fixation, for example, the aforementioned polyurethane, the above-described arcuate cross-section of each deformable barb-like projection 34 (FIG. 3B), can help to stiffen projections 34, in LSR embodiments of component 340, against bending backwards, per arrow BB of FIG. 4B, which backward bending may result in dislodgement of electrodes E1, E2, when a nominal force is applied in a proximal direction to implanted lead 400, for example, in the direction of arrow P in FIG. 4B. Furthermore, to also combat this backward bending in response to the nominal force, angle θ, along which each deformable barb-like projection 34 extends (FIG. 3B) when un-deformed, may be smaller than that which is typical for tines of prior art fixation features, such as tines 141 shown in FIG. 1B, for example, being approximately 30 degrees compared to approximately 45 degrees. The nominal proximal force is of a magnitude that may be inadvertently applied, for example, to connector 43 of lead 400 (FIG. 4A), during the temporary implant of lead 400 for the evaluation of sacral nerve stimulation efficacy, and is lower than that applied to remove lead 400 from the patient's body upon completion of the evaluation.

With further reference to FIG. 3B, according to some exemplary embodiments, a length of each aperture 304 is approximately 0.05 inch (0.05 mm), a width w of each aperture is approximately 0.019 inch (0.482 mm), a length y of each deformable barb-like projection is approximately 0.035 inch (0.889 mm), and a longitudinal spacing S between first ends 314 of adjacent projections 34, within each column, is approximately 0.15 inch (3.81 mm). According to these exemplary embodiments, and with reference to FIG. 3A, a gap g exists between second, free end 342 of each projection 34 and a second edge 324 of the corresponding aperture 304. Those skilled in the art of injection molding will appreciate that gaps g can accommodate interfacing parts of the mold tooling necessary to form component 340 by injection molding. Furthermore, according to the illustrated embodiment and with reference to FIG. 3B, it can be seen that second edge 324 of each aperture 304 tapers away from the corresponding opposing first edge 314, which may also accommodate the tooling necessary for injection molding. Also, as mentioned above, the staggered arrangement of projections 34, which increases an area of the wall section of tubular sidewall 313 that surrounds each aperture 304, can facilitate the molding of component 340.

Finally, with reference back to FIGS. 1A-B, it may be appreciated that both the handling and the assembly, onto a body of an implantable medical device, of a plurality of individual components to form a fixation feature for the device, for example, like tined components 14 onto body 11 of medical electrical lead 200 to form feature 149, can be somewhat tedious, particularly in the manufacture of relatively low profile devices, like temporary implantable medical electrical leads, in which the individual components need to be relatively small in size. Also, in a relatively high volume production run, maintaining, from device to device, a consistent spacing between each of the plurality of individual parts that form the fixation feature can involve a number of assembly steps that may lead to a relatively high cost of manufacturing. Thus, some of advantages of employing a single component having a pre-formed spacing of fixation elements, for example, like any of the embodiments of fixation component 340 described herein, to form the fixation feature of each implantable medical device, are related to increasing the ease of handling the single larger fixation component for each device (versus handling a plurality of smaller fixation components for each device), and related to eliminating assembly steps that are necessary to consistently space a plurality of individual fixation components apart from one another along the body of each device. For example, according to some methods of manufacturing temporary implantable medical electrical lead 400, once conductor coil 45 has been formed, tubular members 471, 472 and fixation component 340 are mounted around coil 45 and positioned, with respect to one another and with respect to one of the terminal ends of coil 45, as illustrated in FIG. 4A, after which tubular members 471, 472 are heat shrunk to secure fixation component 340 directly over the outer surface of conductor coil 45.

In the foregoing detailed description of the disclosure, specific exemplary embodiments of the invention have been described. However, it may be appreciated that various modifications and changes can be made, without departing from the scope of the disclosure, as set forth in the appended claims.

We claim:

1. A fixation component for a medical electrical lead, the component comprising:
   an elongate tubular sidewall including an inner surface and an outer surface, the inner surface defining an elongate lumen that has a uniform diameter along an entire length of the component, to receive a body of the lead, and the outer surface including a central portion and two end portions extending longitudinally from either end of the central portion, the two end portions having a diameter that is less than that of the central portion;
   a plurality of deformable barb-like projections being spaced apart from one another along a length of the central portion of the outer surface of the tubular sidewall, each projection including a first end attached to the tubular sidewall and a second, free end spaced apart from the outer surface of the tubular sidewall, when un-deformed; and
   an aperture corresponding to each of the plurality of barb-like projections, each aperture extending through the elongate tubular sidewall from the central portion of the outer surface to the inner surface, and each aperture having a width and a length, the length of each aperture being defined from a first edge thereof to an opposing second edge thereof, the first edge of each aperture being located in proximity to the attached end of the corresponding projection, and the length and the width of each aperture being sized so that each aperture receives the corresponding projection therein, when the projection is deformed wherein each of the plurality of barb-like projections has an arcuate cross-section that curves in a direction approximately orthogonal to an extension thereof between the corresponding first and second ends, so that each projection has a concave inner surface facing toward the corresponding aperture and a convex outer surface facing away from the aperture.

2. The component of claim 1, wherein the plurality of barb-like projections are arranged in at least one longitudinally extending column, such that each projection of each of the at least one column extends outward in the same general direction.

3. The component of claim 2, wherein the at least one column of barb-like projections includes a first column and a second column, the first and second columns being displaced circumferentially from one another and longitudinally from one another resulting in a staggered arrangement of the plurality of barb-like projections.

4. The component of claim 1, wherein the length of the central portion of the outer surface of the tubular sidewall is greater than approximately 0.5 inch (12.7 mm).

5. The component of claim 1, wherein a length of each end portion of the outer surface of the tubular sidewall is approximately 0.1 inch (2.54 mm) and the diameter of each of the end portions of the outer surface is approximately 0.005 inch (0.127 mm) less than that of the central portion.

6. The component of claim 1, wherein the length of each aperture is greater than a length of the corresponding barb-like projection, from the first end thereof to the second end thereof.

7. The component of claim 1, wherein the second edge of each aperture tapers away from the corresponding opposing first edge.

8. The component of claim 1, wherein the second, free end of each of the plurality of barb-like projections is tapered.

9. The component of claim 1, wherein an entirety of the component is formed from liquid silicone rubber.

10. An implantable medical electrical lead comprising:
a proximal connector terminal;
a distal electrode;
an elongate body formed at least in part by a conductor that extends between the proximal connector terminal and the distal electrode and electrically couples the connector terminal to the distal electrode; and
a fixation component according to claim 1 mounted around the elongate body in proximity to and proximal to the electrode wherein each of the plurality of barb-like projections has an arcuate cross-section that curves in a direction approximately orthogonal to an extension thereof between the corresponding first and second ends, so that each projection has a concave inner surface facing toward the corresponding aperture and a convex outer surface facing away from the aperture.

11. The lead of claim 10, wherein the plurality of barb-like projections of the fixation component are arranged in a first longitudinally extending column and a second longitudinally extending column, the first and second columns being displaced circumferentially from one another and longitudinally from one another resulting in a staggered arrangement of the plurality of barb-like projections.

12. The lead of claim 10, wherein the length of the central portion of the outer surface of the tubular sidewall of the fixation component is greater than approximately 0.5 inch (12.7 mm).

13. The lead of claim 10, wherein the second edge of each aperture of the fixation component tapers away from the corresponding opposing first edge.

14. The lead of claim 10, wherein the second, free end of each of the plurality of barb-like projections of the fixation component is tapered.

15. The lead of claim 10, wherein an entirety of the fixation component is formed from liquid silicone rubber.

16. A temporary implantable medical electrical lead comprising:
a proximal connector terminal;
one or more distal electrodes;
an elongate body formed, at least in part, by a conductor coil that extends between the proximal connector terminal and the one or more distal electrodes and electrically couples the connector terminal to the one or more electrodes, the conductor coil including one or more wound wire filars, each wire filar including an insulative layer for electrical isolation; and
a fixation component directly overlaying an outer surface of the conductor coil in proximity to and proximal to the one or more distal electrodes, the fixation component including an elongate tubular sidewall, a plurality of deformable barb-like projections extending outward from an outer surface of the tubular sidewall, and an aperture corresponding to each projection and extending through the sidewall, each projection including a first end attached to the sidewall in proximity to an edge of the corresponding aperture, and a second, free end spaced apart from the outer surface of the sidewall, when un-deformed, and each aperture exposing the overlaid conductor coil to an environment outside the outer surface of the tubular sidewall of the fixation component.

17. The lead of claim 16, further comprising:
a pair of tubular members closely conforming to the outer surface of the tubular sidewall of the fixation component and to the outer surface of the conductor coil; and
wherein the outer surface of the tubular sidewall of the fixation component includes a central portion, a proximal end portion and a distal end portion, the proximal and distal end portions extending from either end of the central portion;
a first of the pair of tubular members overlaps the proximal end portion of the outer surface of the fixation component and a portion of the outer surface of the conductor coil that extends proximally from the proximal end portion; and
a second of the pair of tubular members overlaps the distal end portion of the outer surface of the fixation component and another portion of the outer surface of the conductor coil that extends distally from the distal end portion.

18. The lead of claim 17, wherein the closely conforming tubular members do not overlap the central portion of the outer surface of the tubular sidewall of the fixation component, and an outer surface of each of the closely conforming tubular members is approximately flush with the central portion of the outer surface of the central portion.

19. The lead of claim 17, wherein:
a length of the central portion of the outer surface of the tubular sidewall of the fixation component is greater than approximately 0.5 inch (12.7 mm); and
the plurality of deformable barb-like projections of the fixation component are spaced apart from one another along the length of the central portion.

20. The lead of claim 17, wherein:
an entirety of the fixation component is formed by molded liquid silicone rubber; and
each of the pair of closely conforming tubular members is formed by heat shrinkable polyester tubing.

21. The lead of claim 17, wherein:
the first of the pair of tubular members includes a proximal terminal end and extends proximally from the proximal end portion of the outer surface of the fixation component over the portion of the outer surface of the conductor coil to the proximal terminal end; and
another portion of the outer surface of the conductor coil, just proximal to the proximal terminal end of the first of the pair of tubular members is exposed to the environment outside the outer surface of the fixation component.

22. The lead of claim 16, wherein the plurality of barb-like projections of the fixation component are arranged in at least one longitudinally extending column, such that each projection of each of the at least one column extends outward in the same general direction.

23. The lead of claim 22, wherein the at least one column of barb-like projections includes a first column and a second column, the first and second columns being displaced circumferentially from one another and longitudinally from one another resulting in a staggered arrangement of the plurality of barb-like projections.

24. The lead of claim 16, wherein a perimeter of each aperture of the fixation component is sized to receive the corresponding deformable barb-like projection therein, when the projection is deformed.

25. The lead of claim 24, wherein a length of each aperture, from the edge, in the proximity of which the first end of the corresponding deformable barb-like projection is attached, to an opposing edge, is greater than a length of the corresponding projection from the first end thereof to the second end thereof.

\* \* \* \* \*